United States Patent

Münzenberg et al.

Patent Number: 5,859,275
Date of Patent: Jan. 12, 1999

[54] PROCESS FOR THE PRODUCTION OF BIS (SILYORGANYL) POLYSULPHANES

[75] Inventors: Jörg Münzenberg, Hanau; Peter Panster, Rodenebach; Matthias Prinz, Freigericht, all of Germany

[73] Assignee: Degussa Aktiengesellschaft, Germany

[21] Appl. No.: 986,238

[22] Filed: Dec. 5, 1997

[30] Foreign Application Priority Data

Dec. 13, 1996 [DE] Germany .................. 196 51 849.0

[51] Int. Cl.$^6$ ........................................... C07F 7/08
[52] U.S. Cl. ............................................ 556/427
[58] Field of Search ............................... 556/427

[56] References Cited

U.S. PATENT DOCUMENTS

| | | | |
|---|---|---|---|
| 5,468,893 | 11/1995 | Parker et al. | 556/427 |
| 5,583,245 | 12/1996 | Parker et al. | 556/427 |
| 5,596,116 | 1/1997 | Childress et al. | 556/427 |
| 5,663,396 | 9/1997 | Musleve et al. | 556/427 |

*Primary Examiner*—Paul F. Shaver
*Attorney, Agent, or Firm*—Beveridge, DeGrandi, Weilacher & Young, LLP

[57] ABSTRACT

A process for the production of bis(silylorganyl)-polysulphanes of the formula $$(R^1R^2R^3SiR^4)_2S_x \quad (I)$$

in which

R$^1$, R$^2$, R$^3$: can be identical or different from each other, and are branched and unbranched alkyl and/or is an alkoxy groups with 1 to 8 cations, wherein at least one alkoxy group is present, aryl residues, in particular phenyl, toluyl, benzyl;

R$^4$: means a divalent alkylidene residue having a chain length of 1–8 C atoms, or —(CH$_2$)$_n$—C$_6$H$_4$—(CH$_2$)$_n$—(n=1 to 4);

by reacting haloalkylalkoxysilanes or haloalkoxysilanes of the formula $$R^1R^2R^3SiR^4X \quad (II)$$

with a polysulphide of the formula $$M_2S_x \quad (III).$$

In a first stage of the reaction, dehydrated polysulphide is obtained by reacting a sulphide hydrate containing water of crystallization with sulphur under a vacuum at a temperature of 60° to 300° C.

9 Claims, No Drawings

PROCESS FOR THE PRODUCTION OF BIS (SILYORGANYL) POLYSULPHANES

INTRODUCTION AND BACKGROUND

The present invention relates to a process for the production of polysulphide silanes using an inorganic polysulphide produced in a novel manner. In another aspect, the present invention relates to a method of producing inorganic polysulphides.

The use of bis(triethoxysilylpropyl)tetrasulphane combined with silicas having an elevated surface area in order to improve the properties of automotive tires, such as abrasion, wet skidding resistance and rolling resistance is prior art which has been documented in numerous patent applications. The difunctional silane here in the above compound acts as a bridge between the hydrophilic inorganic filler, silica, and the hydrophobic organic polymer, wherein a strong covalent bond is formed between the filler and the polymer.

The silylalkylpolysulphanes are essentially produced by nucleophilic substitution on chloroalkylsilanes with anionic polysulphides produced by various methods. Such a process was first described in German patent DE 2141159, but this document gives no information relating to the production of the nucleophilic polysulphide. However, production of the nucleophilic polysulphide is the critical part of the process which gives rise to silylalkylpolysulphanes.

Some patents have described the use of hydrogen sulphides to produce the precursor polysulphide. The German patent DE 2542534 accordingly proposes a method for the production of bis(silylalkyl)polysulphanes in which the polysulphide is formed in situ from hydrogen sulphide and sulphur in alcohol. Hydrogen sulphide is liberated in this process and must be disposed of by suitable measures. This disposal entails additional, economically undesirable, capital costs for an industrial plant. While liberation of hydrogen sulphide may indeed be suppressed by adding alkoxides (German patents DE 2712866 and German published application DE-OS 3311340), this approach is disadvantageous for technical and economic reasons.

Firstly, the anhydrous hydrogen sulphide required for performance of this process must be obtained in a preceding process stage, for example by a reaction between alkoxides and hydrogen sulphide (c.f. U.S. Pat. No. 5,399,739). Hydrogen sulphide, being a highly toxic gas, constitutes a considerable safety hazard, which must be minimized at some cost by suitable technical measures. Furthermore, most alkoxides have only limited storage stability, so entailing continuous in situ production. This additional starting product thus considerably increases the production costs of the desired bis(silylalkyl)polysulphanes.

One possibility for producing the nucleophilic polysulphide is to react sulphide with sulphur. U.S. Pat. Nos. 5,405,985 and 5,468,893 and application EP-A 694552 propose processes which obtain the corresponding polysulphide in an aqueous solution from sulphides and sulphur and react it with haloalkylsilanes in a two-phase system by phase transfer catalysis to yield polysulphanes. In this method, the phase transfer catalyst remains in the product thereby exerting an as yet unexplained influence on the applicational properties of the bis(silylalkyl)polysulphanes. Furthermore, due to the known susceptibility to hydrolysis of the alkoxysilanes used, the products are distinguished, as may be expected, by poor storage stability, thereby further restricting the customer's processing options. For these reasons, two-phase synthesis with a polysulphide produced in an aqueous solution is clearly not an acceptable approach.

There are thus reasons for using anhydrous polysulphide for the reaction between inorganic polysulphide and alkoxysilane. The problem then arises that anhydrous sulphides are not commercially available.

Japanese published patent application JP 7-228588 proposes two processes for the production of a polysulphide to solve this problem. In the first process, a hydrous sodium sulphide is dissolved in a solvent mixture and the water of crystallization present therein is removed by azeotropic distillation of the solvent. In the second method, once drying has been performed under a vacuum, the sodium sulphide is reacted with sulphur in anhydrous ethanol.

Very long reaction times of 5 hours are required for synthesis of polysulphides from sulphides and sulphur in boiling alcohol. This is substantially because sodium sulphide and sulphur have only very limited solubility in the solvents used. Diffusion of the two reactants towards each other thus becomes a determining factor for the rate of reaction. Were the proposed process scaled up to the industrial scale, it is to be suspected that this reaction time would be still longer.

However, with regard to increasing the space/time yield and thus for ensuring better utilization of capital investment, it is necessary to shorten the reaction time in order to achieve an economically viable reaction. The sodium polysulphide is furthermore obtained in the form of alcoholic solutions/dispersions. This proves to be very disadvantageous if further processing and production are not performed on the same site.

It is therefore an object of the present invention to avoid the prior art problems and to provide a process which yields a dehydrated, solid product with shorter reaction times.

SUMMARY OF THE INVENTION

The above and other objects of the invention are achieved by a process for the production of bis(silylorganyl)-polysulphanes of the formula $$(R^1R^2R^3SiR^4)_2S_x \quad (I)$$

in which

R$^1$, R$^2$, R$^3$: are identical or different from each other, and are branched and unbranched alkyl and/or alkoxy groups having a chain length of 1–8 C atoms, wherein at least one alkoxy group is present, aryl residues, in particular phenyl, toluyl, benzyl;

R$_4$: is a divalent alkylidene residue having a chain length of 1–8 C atoms, preferably 1 to 4 C atoms or $$-(CH_2)_n-C_6H_4-(CH_2)_n-(n=1 \text{ to } 4);$$

x is a whole number >1, preferably from 2 to 8, in particular from 2 to 6, by reacting haloalkyl alkoxysilanes or haloalkoxysilanes of the formula $$R^1R^2R^3SiR^4 \quad (II)$$

in which

R$^1$, R$^2$, R$^3$R$^4$ have the same meaning as in formula (I) and x designates a halogen atom such as Cl, Br or I, with a polysulphide of the formula $$M_2S_x \quad (III)$$

wherein

M denotes an alkali metal cation, half an alkaline earth metal or zinc cation and x denotes a number from 2 to 8, in particular from 2 to 6.

In a first reaction stage of the process of the invention a dehydrated polysulphide according to the formula (III) is obtained by a reacting sulphide containing water of crystallization (sulphide hydrates) of the general formula $$M_2S_{x-z} \qquad (IV)$$

in which M and x have the same meanings as above, z designates a number from 1 to 7 and (x–z) is $\geq 1$, with sulphur in the absence of an organic solvent under a vacuum at a temperature of 60° to 300° C.

Suitable ducts for the dehydrated polysulphides are any inorganic sulphides containing water of crystallization, preferably a sodium sulphide. This substance is in particular offered for sale commercially with an $Na_2S$ content of 60–62% and is particularly suitable in this form as a raw material for the process according to the invention.

DETAILED DESCRIPTION OF INVENTION

The following is a more detailed description of the invention. The temperatures and pressures necessary for dehydration and simultaneous polysulphide production are not critical to the performance of the invention, provided that they are adequate to dehydrate the sulphide used. In general, temperatures of 60°–300° C. at a vacuum of between $0.6 \cdot 10^2$ and $70 \cdot 10^2$ Pa are adequate. At temperatures above the phase transition temperature of the sulphide used, the sulphide initially dissolves in the liberated water of crystallization, which is perceived as "melting" of the material. As dehydration proceeds, solid polysulphides or a mixture of polysulphides are obtained, in which the average length of the polysulphane chain assumes a value of >1 to 8, which adheres to the dryer walls and must thus be removed mechanically. In a preferred embodiment of the invention, this "melting operation" is avoided by using temperatures of below the phase transition temperature. As dehydration proceeds, the temperature may gradually be increased as the phase transition temperature rises due to the falling content of water of crystallization, until a dehydrated polysulphide is obtained.

The vacuum required for performance of the invention is temperature-dependent. The higher is the selected temperature, the higher are the admissible pressures. It is appropriate, in order to shorten the dehydration/synthesis time, to use the lowest possible pressures. In a preferred embodiment of the invention, a vacuum of $40 \cdot 10^2$ Pa is used.

The ratio of sulphide hydrate to S may be selected such that a wide range of polysulphides having the formula $M_2S_x$ is covered. One equivalent of sulphide hydrate and n(x–1) equivalents of sulphur are required for a desired polysulphide represented by the formula $M_2S_x$. According to the invention, the factor n may vary between stoichiometric quantities of sulphur (n=1) and a slight excess or deficit of sulphur ($1 \leq n \leq 1.1$). Bis(silylalkyl)polysulphanes are synthesized using polysulphides having more than one S atom (x>1), between 2 and 8 S atoms ($2 \leq x \leq 8$). The water content thereof achievable according to the invention and suitable for the reaction ranges from 0 to 10 wt. %, in particular up to 6 wt. %.

The polysulphide according to the formula (III) produced in the combined dehydration and synthesis stage is then reacted with halosilanes according to the formula (II) in an inert polar solvent or solvent mixture.

The reaction components halosilane according to the formula (II) and the polysulphides according to the formula (III) may be introduced together into a solvent or solvent mixture and reacted, or one of the two reactants is apportioned as such or as a solution to the second reaction component. The second reaction component may also be present as the substance or as a solution. It is not critical to performance of the process according to the invention which of the two reactants is initially introduced and which is apportioned.

The polysulphide production which precedes the actual production of the bis(silylorganyl)polysulphides results in a considerable shortening of cycle times and makes this process particularly economic.

In a preferred embodiment of the invention, both reactants according to the formulae (II) and (III) are initially introduced into an inert solvent or solvent mixture and then reacted.

Solvents or components of a solvent mixture which may be considered are ethers such as diethyl ether, diisopropyl ether, dibutyl ether, methyl tert.-butyl ether, tetrahydrofuran, dioxane, dimethoxyethane or diethoxyethane, alcohols such as methanol, ethanol, propanol and ethylene glycol together with aliphatic or aromatic hydrocarbons such as pentane, hexane, heptane, petroleum ether, benzene, toluene or xylene. Preferred solvents are alcohols, wherein in a particularly preferred embodiment of the invention, the alcohol used corresponds to that of the alkoxy group attached to the alkoxysilyl group.

The reaction solution is heated to a temperature of between 40° C. and the boiling point of the reaction mixture in order to accelerate the reaction between the chloroalkylsilane and the polysulphides. A reaction temperature close to the boiling point of the reaction mixture is preferably used.

The pressure prevailing during the reaction is not critical to performance of this invention, provided that it allows reaction temperatures of above 40° C.

Reaction time is dependent upon reaction temperature. The higher is the reaction temperature, the shorter is the time required for completion of the reaction. Reaction times of 1 to 8 hours are generally sufficient.

Once the reaction is complete, the reaction mixture is filtered in order to remove the precipitated insoluble halides. The solvent or solvent mixture is separated from the filtrate. To this end, the product mixture is heated to a temperature above the boiling temperature of the solvent or solvent mixture, which is distilled off. In a preferred embodiment, the solvent is removed under a vacuum.

The following Examples illustrate performance of the invention in greater detail.

EXAMPLE 1

Production of bis(3,3'-triethoxysilylpropyl) polysulphane having an average S chain length of 3.7

32.04 g (approx. 0.25 mol) of $Na_2S$ hydrate ($Na_2S$ content 60–62%) are introduced together with 24.05 g (0.75 mol) of sulphur into a 500 ml 3-necked flask fitted with a reflux condenser and heated to 250° C. in a heating mantle under a vacuum of 35 mbar for 1.5 h. The mixture first melts and water is distilled off. After 1.5 h, the melt has solidified. The temperature is reduced, the flask provided with a dropping funnel, $N_2$ purging and a KPG stirrer and charged with 125 ml of ethanol. After heating to reflux, wherein a proportion of the solidified melt passes into solution, 120.4 g (0.5 mol) of 3-chloropropyltriethoxysilane are added dropwise at this temperature within 15 minutes. Refluxing is continued for a further 2 h, wherein the color of the reaction mixture changes from the original dark brown to yellow. After cooling at room temperature, the mixture is pressure-filtered, the filter cake rinsed with 50 ml ethanol and the combined filtrates evaporated in a rotary evaporator at 90° C. and 30 mbar. 121.51 g (0.23 mol) of a polysulphane mixture having an average S chain length of 3.7 are obtained. Yield is 92%. The identity of the mixture is confirmed by the $^1$H-NMR spectrum.

EXAMPLE 2

Production of bis(3,3'triethoxysilylpropyl) polysulphane having an average S chain length of 3.7

32.04 g (approx. 0.25 mol) of Na$_2$S hydrate (60–62% Na$_2$S) are introduced together with 24.05 g (0.75 mol) of sulphur into a notched 1000 ml flask and, under a vacuum of 13 mbar, exposed to the following temperature profilee in a rotary evaporator:

15 min 90° C.
30 min 100° C.
30 min 110° C.
60 min 140° C.

The resultant sodium polysulphide, which did not melt during dehydration, is transferred into a three-necked flask. After addition of 125 ml of ethanol and 120.4 g of 3-chloropropyltriethoxysilane, the mixture is refluxed for 2 h in a 500 ml three-necked flask provided with a reflux condenser and N$_2$ purging. The temperature is reduced to room temperature, the precipitate filtered out and the filter cake washed with 50 ml of ethanol. Once the solvent has been distilled off from the combined filtrates in a rotary evaporator at 90° C. and a vacuum of 30 mbar, a little precipitate must again be filtered out. 120.90 g (0.23 mol) of a polysulphane mixture having an average S chain length of 3.7 are obtained. Yield is 92%. The identity of the mixture is proven by the $^1$H-NMR spectrum.

EXAMPLE 3

Production of bis(3,3'triethoxysilylpropyl) polysulphane having an average S chain length of 2.0

32.04 g (approx. 0.25 mol) of Na$_2$S hydrate (Na$_2$S content 60–62%) are introduced together with 8.02 g (0.25 mol) of sulphur into the apparatus of Example 1 and heated to 250° C. in a heating mantle for 2 h under a vacuum of 35 mbar. The mixture first melts and water is distilled off. After 2 h, the mixture has solidified. The temperature is reduced, the flask provided with a dropping funnel and a KPG stirrer and charged with 125 ml of ethanol. After heating to reflux, wherein a proportion of the solidified melt passes into solution, 120.4 g (0.5 mol) of 3-chloropropyltriethoxysilane are added dropwise at this temperature within 15 minutes. Refluxing is continued for a further 2 h, wherein the color of the reaction mixture changes from the original orange-yellow to yellow. After cooling at room temperature, the mixture is pressure-filtered, the filter cake rinsed with 50 ml of ethanol and the combined filtrates evaporated in a rotary evaporator at 90° C. and 30 mbar. 99.51 g (0.21 mol) of a polysulphane mixture having an average S chain length of 2.0 are obtained. Yield is 84%. The identity of the mixture is confirmed by the $^1$H-NMR spectrum.

EXAMPLE 4

Production of bis(3,3'triethoxysilylpropyl) polysulphane having an average S chain length of 1.9

32.04 g (approx. 0.25 mol) of Na$_2$S hydrate (60–62% Na$_2$S) are introduced together with 8.02 g (0.25 g) of sulphur into the same apparatus as in Example 2 and, under a vacuum of 13 mbar, exposed to the following temperature profile in a rotary evaporator:

15 min 90° C.
30 min 100° C.
30 min 110° C.
60 min 140° C.

The resultant sodium polysulphide, which did not melt during dehydration, is transferred into a three-necked flask. After addition of 125 ml of ethanol and 120.4 g of 3-chloropropyltriethoxysilane, the mixture is refluxed for 2 h in a 500 ml three-necked flask provided with a reflux condenser and N$_2$ purging. The temperature is reduced to room temperature, the precipitate filtered out and the filter cake washed with 50 ml of ethanol. Once the solvent has been distilled off from the combined filtrates in a rotary evaporator at 90° C. and a vacuum of 30 mbar, a little precipitate must again be filtered out. 97.45 g (0.21 mol) of a polysulphane mixture having an average S chain length of 1.9 are obtained. Yield is 83%. The identity of the mixture is proven by the $^1$H-NMR spectrum.

Further modifications and variations of the foregoing will be apparent to those skilled in the art and are intended to be encompasses by the claims appended hereto.

German priority application 196 51 849.0 is relied on and incorporated herein by reference.

We claim:

1. A process for the production of a bis(silylorganyl) polysulphane of the formula $$(R^1R^2R^3SiR^4)_2S_x \qquad (I)$$

in which $R^1$, $R^2$ $R^3$ are identical or different from each other, and are branched and unbranched alkyl and/or alkoxy groups having a chain length of 1–8 C atoms, wherein at least one alkoxy group is present, aryl residues, in particular phenyl, toluyl, benzyl;

$R^4$ is a divalent alkylidene residue having a chain length of 1–8 C atoms, or $$-(CH_2)_n-C_6H_4-(CH_2)_n- \quad n=1 \text{ to } 4);$$

x means a number >1, comprising reacting a haloalkylalkoxysilane or haloalkoxysilane of the formula $$R^1R^2R^3SiR^4X \qquad (II)$$

in which $R^1$, $R^2$, $R^3R^4$ each have the same meaning as in formula (I) above and X designates a halogen atom with a polysulphide of the formula $$M_2S_x \qquad (III),$$

wherein

M is an alkali metal cation, half an alkaline earth metal or zinc cation and x denotes a number from 2 to 8, where in a first stage a dehydrated polysulphide according to the formula (III) is obtained by reacting a sulphide containing water of crystallization of the formula $$M_2S_{x-z} \qquad (IV)$$

in which M and x have the same meanings as above, z designates a number from 1 to 7 and (x–z) is $\geq 1$, with sulphur in the absence of an organic solvent under a vacuum at a temperature of 60° to 300° C.

2. The process according to claim 1 wherein $R^4$ has 1–8 carbon atoms.

3. The process according to claim 1 wherein x is 2 to 8.

4. The process according to claim 1, where in the first stage $Na_2S$ containing water of crystallization having an $Na_2S$ content of 60 to 62 wt. % is used.

5. The process according to claim 1 wherein a vacuum of between $0.6 \cdot 10^2$ and $70 \cdot 10^2$ Pa is used.

6. The process according to claim 4 wherein a vacuum of between $0.6 \cdot 10^2$ and $70 \cdot 10^2$ Pa is used.

7. The process according to claim 1 wherein one equivalent of the hydrated monosulphide is reacted with $n(x-1)$ equivalents of sulphur, wherein n assumes a value of $1 \leq n \leq 1.1$.

8. The process according to claim 5 wherein one equivalent of the hydrated monosulphide is reacted with $n(x-1)$ equivalents of sulphur, wherein n assumes a value of $1 \leq n \leq 1.1$.

9. The process according to claim 1 wherein the temperature during the reaction to yield the polysulphides is increased as a function of the phase transition temperature of the sulphide hydrates in such a manner that it is always below the particular relevant transition temperature.

* * * * *